United States Patent [19]

Clarke

[11] Patent Number: 4,863,437

[45] Date of Patent: Sep. 5, 1989

[54] MEANS FOR FLUID ADMINISTRATION

[76] Inventor: Ellis W. Clarke, 47 Deramore Drive, Belfast, Northern Ireland

[21] Appl. No.: 27,159

[22] Filed: Mar. 17, 1987

[30] Foreign Application Priority Data

Mar. 20, 1986 [GB] United Kingdom ................. 8607004
May 19, 1986 [GB] United Kingdom ................. 8612076
May 20, 1986 [GB] United Kingdom ................. 8612175

[51] Int. Cl.$^4$ ........................................... A61M 5/005
[52] U.S. Cl. ..................................... 604/246; 604/403; 137/843
[58] Field of Search ................................ 604/245–247, 604/251, 257, 260, 262, 80, 83, 85, 250, 122, 254, 255, 85, 92, 246, 403, 404, 407, 408, 410; 137/843

[56] References Cited

U.S. PATENT DOCUMENTS

| 220,559 | 10/1979 | Wilson | 137/843 |
|---|---|---|---|
| 2,526,331 | 10/1950 | Copping | 137/843 |
| 3,587,313 | 6/1971 | Smith | 604/246 |
| 3,738,361 | 6/1973 | Price | 604/403 |
| 4,043,332 | 8/1977 | Metcalf . | |
| 4,103,686 | 8/1978 | LeFevre . | |
| 4,142,523 | 3/1979 | Stegeman | 604/246 |
| 4,186,740 | 2/1980 | Guerra . | |
| 4,474,574 | 10/1984 | Wolfe et al. | 604/246 |
| 4,556,086 | 12/1985 | Raines | 137/843 |
| 4,613,325 | 9/1986 | Abrams . | |
| 4,684,364 | 8/1987 | Stwyer et al. | 137/843 |

FOREIGN PATENT DOCUMENTS

| 34671 | 2/1981 | European Pat. Off. . | |
|---|---|---|---|
| 2346762 | 10/1977 | France . | |
| WO/8001756 | 9/1980 | PCT Int'l Appl. . | |
| WO/8404460 | 11/1984 | PCT Int'l Appl. . | |
| 438611 | 11/1935 | United Kingdom | 604/246 |
| 1519558 | 8/1978 | United Kingdom . | |
| 2012393 | 7/1979 | United Kingdom . | |
| 1561288 | 2/1980 | United Kingdom . | |
| 647951 | 2/1985 | United Kingdom | 604/251 |

Primary Examiner—John D. Yasko
Attorney, Agent, or Firm—Jacobs & Jacobs

[57] ABSTRACT

An administration set which is suitable for giving an infusion of liquid to a patient by gravity flow from a container of liquid through the set and to the patient comprises a fluid reservoir, a flow regulator and a barostat device which compensates for changes in fluid pressure during the infusion. The fluid reservoir is positioned upstream of the flow regulator and the barostat device is downstream of the flow regulator. In a preferred embodiment a piercing needle connects with a closable tube and injection site which enter the main body of the reservoir by a secure seal. One side of the top of the reservoir extends in a curving manner to be in front of the closable tube and joins an air channel that leads to an airtight chamber which holds the barostat device. An outlet passage leads from the bottom of the reservoir to a collapsible region and descends to an outlet tube which leads via the regulator to the barostat device. A resistive pathway is formed between the ascending and descending parts of the outlet passageway whereby the reservoir may empty slowly when the collapsible region is collapsed. A drip-chamber may be placed in the infusion tube. A collapsible tube is placed downstream of the barostat device.

21 Claims, 5 Drawing Sheets

MEANS FOR FLUID ADMINISTRATION

BACKGROUND OF THE INVENTION

This invention relates to an administration set which is suitable for giving an infusion of fluid to a patient by gravity flow from a fluid container through the administration set to some form of tube which enters the patient. More particularly the invention relates to an administration set which comprises a fluid reservoir, a flow regulator and a barostat device which compensates for changes in pressure during the infusion. Although this invention relates primarily to sets that are used to infuse fluids intravenously it can be employed in other types of fluid administration.

DESCRIPTION OF RELATED ART

A conventional intravenous administration set has a piercing needle that can be inserted into a suitable fluid container through a sterile port. The term fluid is used herein in the commonly used manner as referring to a liquid. The tube leading from the piercing needle usually enters a filter chamber containing a gauze-type filter that is particularly necessary for trapping any clotted material when blood is being infused. The fluid then passes to a calibrated orifice from which it falls in drops through an air space in a drip-chamber so that the rate of flow may be easily observed. A long transparent infusion tube conveys the fluid from the drip-chamber to a hollow needle, cannula or catheter located in a suitable vein, normally in the patient's arm. These devices for providing access to the vein will be referred to simply as the cannula. A flow regulator is located down-stream from the drip-chamber and usually consists of an adjustable clamp which compresses the infusion tube. The fluid container is suspended at a height of about six feet from the floor and may be in the form of a collapsible plastic bag or a rigid bottle. The rigid bottle has an air-inlet with filter that may be incorporated in the piercing needle or consist of a separate hollow needle device. The administration set is made from materials that are neither toxic or pyrogenic, the internal surfaces are kept free from particulate matter and it is normally sterilised by the manufacturer and supplied in a suitable sealed package.

Several difficulties may arise when giving an infusion with the conventional type of administration set. The flow rate may vary because of a varying back-pressure. This back-pressure arises from the pressure of the blood in the arm veins and a resistance to the flow of the infusate as it passes through a constricted vein. This constriction is occasionally severe enough to stop the flow. When using a collapsible container there is also a reduction in the flow rate due to a fall of the pressure head in the container as it empties. Also the fluid container must be observed frequently in order to be sure that it does not become completely empty before being replaced with a full one. If the container does become empty the fluid level will rapidly descent through the set until it reaches an equilibrium point, usually a little above the level of the patient's shoulder, where the pressure generated by the fluid just balances the pressure in the arm veins. Under these circumstances movement of the patient, or the set, can easily cause the patient's blood to flow back into the cannula where it may clot. As the fluid level descends in the infusion tube it draws in air which is then quite difficult to remove. Some of the collapsible plastic containers contain little or no air so that when they are empty the pressure in the system falls until it balances the pressure in the arm veins and again movement of the patient can easily cause blood to flow back into the cannula. Air may also be drawn into the set if the infusion is not stopped when the piercing needle is being transferred from the nearly empty to the full container. Thus the flow is usually stopped for this purpose by closing the regulator and when the flow is re-started it has then to be carefully re-adjusted to give the prescribed rate of flow. It is also necessary that there must be sufficient air in the drip-chamber but this air frequently escapes upwards into the filter-chamber during manipulations such as those associated with changing the fluid container. Replacing this lost air without getting some into the infusion tube can also be a troublesome procedure.

It has been proposed to compensate for flow rate variations caused by changes in venous back pressure and/or fall in the pressure head by employing flexible membranes which move in relation to fixed inlets and outlets in the fluid pathway as the pressure changes, see for example United Kingdom Patents Nos. 2012393 and 1519558. In patent No. 2012393 this membrane is also responsible for setting the rate of flow and therefore has to be adjusted every time it is necessary to change the flow rate. The administration set of the present invention separates these functions whereby the rate may be altered in a simple manner and the barostat device automatically adjusts to the new rate.

United Kingdom Patent No. 1561288 describes a fluid flow rate control device in the form of a straight collapsible conduit which can vary in cross-section according to variations in the transmural pressure difference. None of these patents discloses or suggests the use of a fluid reservoir in combination with a barostat device as required by the present invention.

SUMMARY OF THE INVENTION

The administration set of the present invention mitigates many of the above disadvantages by providing an administration set in which the flow is not significantly affected by some or all of the usual disturbing variations in pressure. Compensation is provided by a barostat device placed downstream of the regulator. This barostat device restricts the flow sufficiently to raise the pressure at its inlet to a pressure that is substantially equal to or differs by a constant amount from, a controlling pressure that is acting on the device. This controlling pressure may be simply the atmospheric pressure. The pressure downstream of a regulator is normally sub-atmospheric by an amount which varies with changes in the back pressures from the veins and by raising this pressure to a constant value near to the atmospheric pressure the barostat device acts in effect as a barrier that prevents all but very large changes in pressure from passing back to the regulator and thus influencing the flow. This process is analogous to the building of a weir to prevent tidal variations in the lower part of a river from affecting the level in the upper part, the higher the weir the greater the degree of protection it provides. The administration set is also adapted to maintain the infusion for a convenient period of time after the fluid container has become empty by the provision of a fluid reservoir upstream of the regulator. The barostat device is preferably placed at the same level as the outlet of the reservoir and this causes the pressure at the outlet of the reservoir as it is emptying to be near the controlling pressure which in this case is the atmospheric pressure. Thus when the container is empty the reservoir empties at a diminishing rate and the flow will finally stop before the reservoir becomes completely empty. This arrangement is analogous to the emptying of say a barrel through a tap placed below the barrel but with its outlet raised to be slightly above the bottom of the barrel. The tap represents the regulator and has the atmospheric pressure downstream of its outlet in the same way that the regulator has downstream at a similar level the atmospheric pressure maintained by the barostat device. This arrangement ensures that a slow infusion is maintained for a considerable time, air does not enter the rest of the administration set even when the reservoir is empty and, because there is still a column of fluid held in the infusion tube by the virtually closed barostat device, blood is unlikely to flow back into the cannula against the pressure generated by this fluid column.

The controlling pressure in the barostat device may be atmospheric pressure plus the pressure generated by the part of the fluid column above the barostat device minus a column in the fluid reservoir. In this case as the container empties the controlling pressure and so the pressure at the inlet of the device and thus the pressure downstream of the regulator becomes reduced by the same amount as the pressure on the upstream side of the regulator which is being generated by the fluid column above a fluid level in the fluid reservoir plus the fluid column below the fluid level in the reservoir. This means that the pressure gradient across the regulator will not change and so the rate of flow will not change until the effective fluid level in the system falls to that of the fluid level in the reservoir. The pressure thus normally propelling the infusion corresponds with the height of the fluid column in the reservoir. This type of barostat device will also act like the previous one by causing the reservoir to empty at a diminishing rate without becoming completely empty and as a barrier that prevents all but very large changes in the back pressure from influencing the pressure gradient across, and thus the flow through, the regulator.

The controlling pressure in the barostat device may be generated by the whole column of fluid above the device. (Specific embodiments of which are described in FIGS. 5 and 6). In order that fluid shall still be able to flow through the device it preferably contains an elastic element that acts on the flexible element in such a way as to oppose the force of the controlling pressure and so cause the pressure at the inlet to the device to be significantly lower by a constant amount than the controlling pressure. This form of barostat device does not cause the reservoir to empty at a diminishing rate and the flow to stop before the reservoir has become completely empty. Other means are used to prevent the reservoir from emptying completely and thus there is no need to place the barostat device at the same level as the lowest part of the reservoir.

The administration set may also provide means for estimating the back pressures or for indicating when the back pressures have become so large that they begin to affect the rate of flow. The administration set may also provide means for preventing air from being lost from the drip-chamber and means for avoiding the need to close the regulator when changing the fluid container. The administration set may also include means at the reservoir inlet for introducing medicaments or for connecting to a secondary container and also be adapted so that the reservoir inlet and an air channel leading to the barostat device may be closed either together or separately.

Accordingly the present invention provides an administration set which comprises a fluid reservoir, a barostat device and a flow regulator in which the fluid reservoir is upstream of the flow regulator and the barostat device is downstream of the flow regulator.

The barostat device influences the flow of a fluid through it in such a way as to cause the pressure of the fluid at its inlet to have a constant relation with that of an externally applied controlling pressure for example the atmosphere. In the present invention in a preferred form of the barostat device the controlling pressure is applied to a flexible element that suitably impedes the flow from its outlet.

According to a second aspect of the present invention there is provided an administration set which comprises a fluid reservoir, a barostat device and a flow regulator in which the barostat device is down-stream from the flow regulator and the fluid reservoir is up-stream from the flow regulator and in which the barostat device comprises a flexible element that is caused by the pressure of the atmosphere to offer the amount of resistance to flow that is required to raise the pressure at its inlet to be near to the atmospheric pressure and in which the fluid reservoir has its outlet at about the same height as the inlet to the barostat device.

Suitably the barostat device and the fluid reservoir may be formed integrally, that is they comprise two parts of a single component of the administration set.

The barostat device may consist simply of a collapsible passageway formed by a short length of thin-walled lay-flat tubing made from a suitable flexible material such as plastics material and these thin walls will then comprise the flexible element. The passageway has an internal cross-section that may vary according to small variations in the transmural pressure and is adapted to close at a collapsing region.

Figure 1:
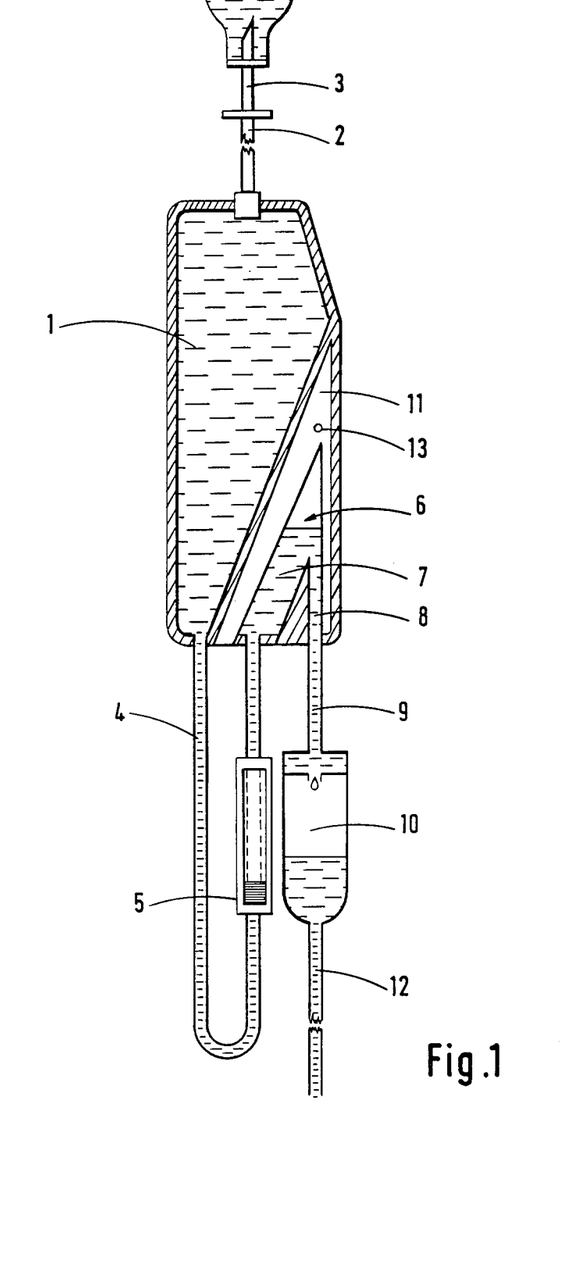
FIG. 1 shows a diagrammatic elevation of an administration set according to the second aspect of the invention.

An embodiment of this aspect is illustrated in FIG. 1 described below. In use the barostat device is preferably placed in the fluid pathway of the administration set about mid-way in vertical distance between the fluid container and the patient's shoulder. When the flow regulator is set to restrict the flow, a sub-atmospheric pressure will develop in the column of fluid downstream from the regulator and so within the barostat device. The atmospheric pressure pressing on the flexible walls of the barostat device will thus hold them in close opposition and cause them to offer a resistance to the flow that is sufficient to raise the pressure at the inlet of the device to a pressure which may differ by a small and constant amount from the atmospheric pressure and will be called the closing pressure. Fluid passing through the regulator will cause the pressure at the inlet of the barostat device to rise slightly above the closing pressure and the flexible walls to open sufficiently to allow this small volume to flow through the device and onwards to the patient. The normal high resistance of the barostat device serves to divide the fluid column into an upper and a lower part. Only the upper part provides the force that propels the fluid through the regulator and so together with the regulator determines the rate of flow of the infusion. The pressure generated by the lower part of the fluid column is normally more than sufficient to overcome the back pressure caused by a constriction of the cannulated vein and the arm vein blood pressure and so prevents them from significantly affecting the pressure in the upper part and thus the pressure gradient across the regulator; therefore the rate of flow remains relatively constant. If the back pressure in the lower column is varied experimentally by for example raising or lowering the level of the outlet of the cannula only minor changes, of between ±5% are observed in the rate of flow. If the back-pressures do exceed the pressure provided by the lower part of the fluid column the flexible walls of the barostat device will open widely and any further build up of back-pressures will start to reduce the pressure head in the upper part and reduce the rate of flow of the infusion. Such a wide opening of the walls of the barostat device can be arranged to provide a visible, or palpable, warning that a high back-pressure exists and is interferring with the flow.

Suitably the barostat may have its collapsible passageway formed in an inverted U or V-shape with its inlet and outlet passages arranged close together. The use of passages so arranged means that any distortion of the surrounding flexible structures will cause less disturbance of the collapsing region of the device. If for example the inlet and outlet passages were more widely separated or diametrically opposed, as would occur if the collapsible passageway were straight, the collapsing region would be more likely to become distorted so altering the closing pressure and thus the compensating characteristics of the device.

The reservoir provided up-stream of the flow regulator has preferably flexible collapsible walls and, after the fluid container has become empty, continues to supply fluid to the patient at a slow rate. The inlet to the barostat device is preferably arranged to be at or to be effectively at the same height with respect to emptying as the outlet to the reservoir in order to prevent the reservoir from emptying completely and to cause the rate of flow to become very slow. The flow eventually stops when the pressure head generated by the difference in height between the fluid level in the reservoir and the inlet to the barostat device, plus the atmospheric pressure, just equals the closing pressure. In the case of a typical infusion, where the regulator is set to administer say three liters a day, a reservoir with a capacity of only thirty milliliters can maintain this reduced flow for about three hours after the container has emptied. As the reservoir cannot empty completely because of the position of the barostat inlet, air is prevented from entering the infusion tube. When the flow has finally stopped blood is unlikely to flow back into the cannula since this would require the pressure of the blood in the veins to exceed that being generated by the column of fluid in the lower part of the fluid column below the barostat device. The reservoir fills again automatically when the empty fluid container is replaced by a full one and there is no need to close the regulator and thus disturb its setting. The tube connecting the outlet of the reservoir with the inlet of the barostat device must contain the flow regulator and could also contain a drip-chamber. It is convenient to arrange this tube as a hanging U-shaped or double S-shaped loop. This loop can then trap any air that may escape upwards from the drip-chamber. Such an escape may occur for example after the fluid container has been squeezed sufficiently to compress the air in the drip-chamber and cause the fluid to squirt into it. The air is carried back to the drip-chamber when forward flow is resumed. The drip-chamber can also be placed downstream of the barostat device and here too any escape of air is trapped and returned by the forward flow.

A fine gauze filter is normally required for filtering out any unsuitable particulate matter and may be placed immediately downstream of the piercing needle or within the body of the drip chamber.

When the administration set provided by this second aspect of the invention is used with the collapsible type of fluid container the rate of flow of the infusion will still become reduced by the reduction in the pressure head in the upper part of the fluid column as the container empties. This change in pressure head and flow may be considerably reduced by supporting the collapsible container horizontally by means of a suitably designed sling or through-shaped platform.

In a third aspect the present invention modifies the administration set described hereinbefore so that, when it is used with the collapsible type of fluid container, the flow rate will remain substantially unaffected as the container empties. In this aspect the administration set is adapted to enable of the part of the fluid column above the barostat device to be shortened, with a lengthening of the part below, and thus to provide an increase in the pressure head available to compensate for changes in back pressure from the veins. The stability of the barostat device is also increased and a convenient means for estimating the back pressure is provided.

Figure 2:
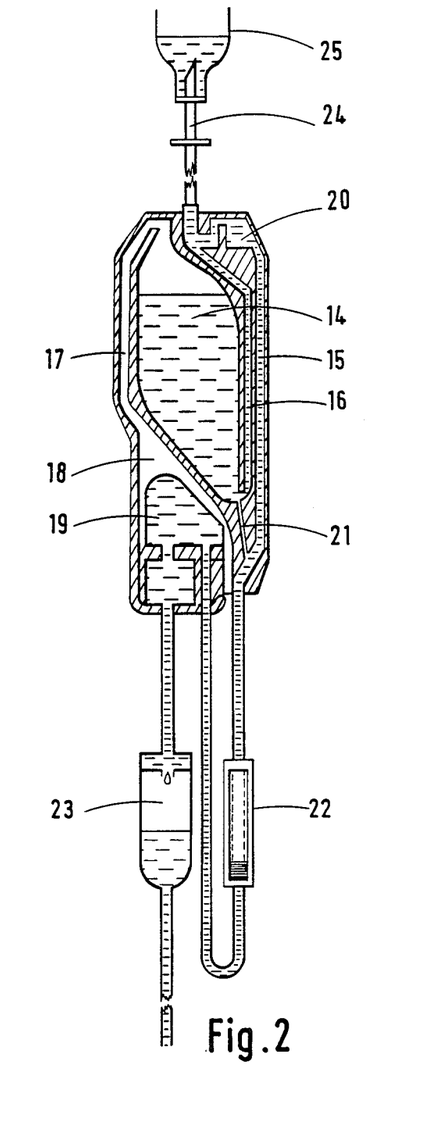
FIG. 2 shows a similar view of an administration set according to the third aspect of the invention.
Figure 2A:
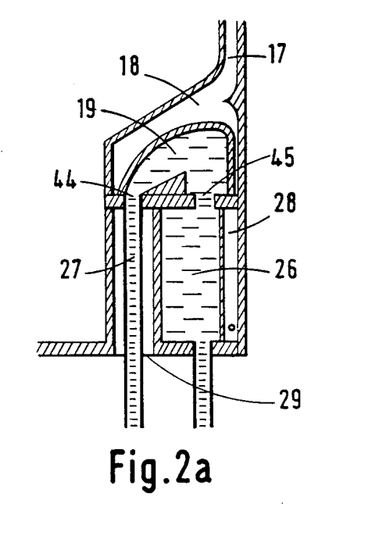
FIG. 2a shows a enlarged diagrammatic view of the barostat device used in the third and fourth aspects of the present invention.

An embodiment of this aspect of the invention is illustrated in FIGS. 2 and 2a described below.

According to a third aspect of the present invention there is provided an administration set arranged substantially as hereinbefore described in which the flexible element of the barostat device is caused by the pressure of air in the reservoir to offer the amount of resistance to the flow of fluid through the barostat device that is required to raise the pressure at its inlet to that of the atmosphere plus the pressure generated by the part of the fluid column above the barostat device minus the column in the fluid reservoir, a by-pass tube that allows the fluid to by-pass the fluid reservoir, a collapsible region at the uppermost part of the by-pass tube and a resistive pathway providing an alternative outlet from the fluid reservoir.

Suitably a collapsible tube may be placed downstream from the barostat device.

The fluid reservoir is now placed immediately below the piercing needle. A passage conveys fluid from the piercing needle to the lower part of the reservoir. This arrangement ensures that the incoming fluid traps the air initially present in the reservoir in its upper part. The barostat device is still placed at the level of the outlet from the reservoir but the air pressing on its flexible element is not at the atmospheric pressure but is contained in an air-tight chamber that communicates via an air channel with the air trapped in the top of the fluid reservoir. If a collapsible type of fluid container is being used the pressure of the fluid upstream of the regulator becomes reduced as the container empties. A similar reduction of pressure occurs in the fluid and air in the reservoir. This reduction of pressure in the reservoir is transmitted via the air channel to the flexible element of the barostat device and reduces the pressure at its inlet which, as it is down-stream of the flow regulator, causes the pressure difference across the regulator, and thus the flow, to remain constant. The by-pass tube conveys fluid directly from the piercing needle to the tube leading to the regulator and when the fluid container becomes empty a collapsible segment or region at the upper most part of the by-pass tube collapses and prevents the flow of either air from the container or the fluid that would otherwise syphon over from the fluid reservoir. When the collapsible region collapses the reservoir can only empty slowly through the resistive pathway into the tube leading to the regulator and may maintain the flow through the system for several hours even when the regulator is set to give a high rate of flow.

The barostat device should maintain at its inlet a pressure that is similar to, and will vary with, the controlling pressure applied to its flexible element, providing these pressures are greater than at the outlet. Ideally the inlet pressure should not vary with changes in the outlet pressure. The type of barostat device consisting of a collapsible passageway is more affected by changes in the outlet pressure. A simple way of making the inlet pressure of such a device independent of the outlet pressure is to place a collapsible tube down-stream from the device. This collapsible tube is exposed to the atmospheric pressure and in effect separates the outlet pressure of the barostat device from the down-stream changes by keeping it constant at near to the atmospheric pressure. If the back-pressure becomes great enough to reduce the pressure across the regulator and thus the rate of flow it will be greater than the atmospheric pressure in the region of the collapsible tube and will cause the thin walls to become distended. Squeezing this distended collapsible tube briefly will be followed by a reversed flow in the drip tube of the drip chamber, in the same way as occurs in the previous aspect of the invention after squeezing the collapsible passageway of the barostat, and so wil provide an indication that the back-pressure is impeding the flow.

If the collapsible tube made from 30 to 40 centimeters in length and replaces the upper part of the infusion tube it can provide a means for measuring the amount of the back-pressure from the veins. This long form of collapsible tube will remain collapsed down to the level of the top of what can be regarded as a column of fluid that is being supported by the back-pressure from the veins. Below this level the collapsible tube will be distended and the transition from the collapsed to distended state is easily determined, even in a dimly lit ward, by gently feeling the tube between finger and thumb. The nurse can thus measure the amount of back-pressure and so follow its development rather than, as in the previous form of the invention, only be warned when the pressure was so high that it was interfering with the flow. This long form of collapsible tube can also function as the barostat device in the previous aspect of the invention where the flexible element is being influenced by the atmospheric pressure rather than by the pressure in the reservoir.

Figure 3:
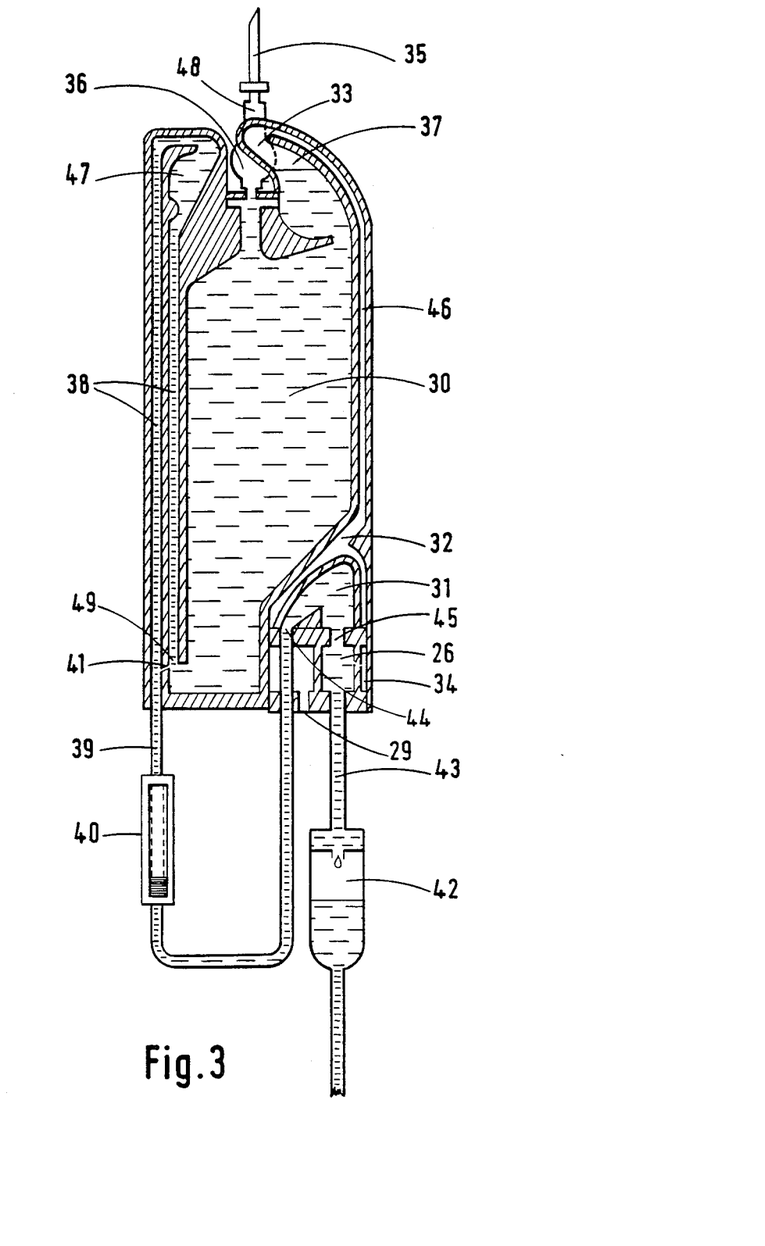
FIG. 3 shows a similar view of an administration set according to the fourth aspect of the invention.
Figure 4:
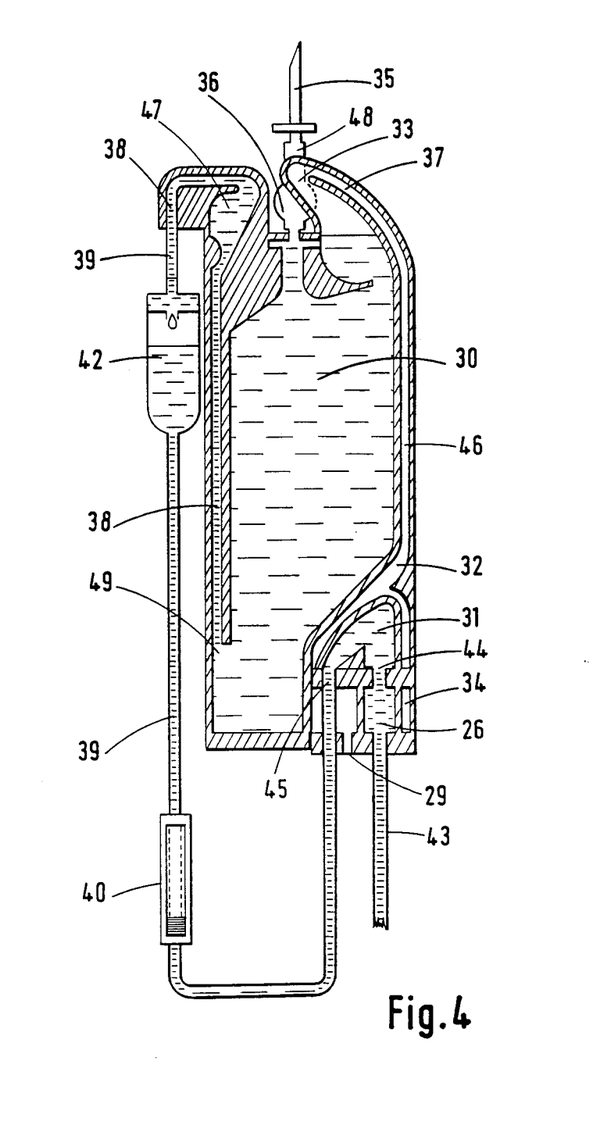
FIG. 4 shows a similar view of an alternative embodiment of an administration set according to a fourth aspect of the invention.

In another aspect of the present invention the administration set described hereinbefore may be adapted so that drugs and other substances may be introduced into the reservoir and also so that the inlet to the reservoir may be closed to prevent spillage when the piercing needle is being transferred to another container. In this aspect of the invention the administration set may also be adapted so as to enable the barostat device to be rendered temporarily inoperative so that it becomes possible to increase the pressure in the reservoir and so to cause a considerably increased rate of flow. An embodiment of this aspect of the invention is illustrated in FIGS. 3 and 4 described below.

According to this fourth aspect of the present invention there is provided an administration set made in a similar way to that in the third aspect but in which the fluid flows from the piercing needle directly into the main body of the reservoir via a closable tube and injection site, a part of the reservoir is extended upwards to join the air channel at a closable region beside the closable tube, an outlet tube passes upwards from the lower part of the reservoir to a collapsible segment then downwards to the regulator, a resistive pathway by-passes the collapsible segment and a drip chamber is placed either up-stream of the regulator or down-stream of the barostat device.

In this aspect of the invention the reservoir forms part of the fluid pathway from the fluid container to the patient and so drugs or other substances may be added to the reservoir for administration to the patient. For example some of the fluid in the reservoir could be squeezed back into the container and a clamp used to close the closable tube leading from the piercing needle to the reservoir. An injection of say a drug is then made through a rubber injection site down-stream of the clamp and the reservoir squeezed several times to thoroughly mix the drug with the fluid remaining in the reservoir. The infusion is resumed at its previous rate when the clamp is removed and the drug may then be administered in a controlled fashion.

If a larger volume of a drug solution or other material needs to be infused this can be dispensed from a secondary container. This is infused by means of a supplementary set consisting of a piercing needle and a short length of tubing connecting it to a short narrow, sharpened hollow needle. The closable tube is clamped, as before, and the short needle inserted fully through the injection site below the clamp. The piercing needle of the supplementary set is then inserted into the outlet part of the secondary container which is then suspended from the hook that is being used to support the primary container. The infusion may now proceed exactly as before but with the fluid from the secondary container. When the secondary container is empty the reservoir will again maintain a flow at a reduced rate via the resistive pathway. The nurse can then, at her convenience, remove the empty secondary container and, if she needs to infuse the previous solution, simply remove the supplementary set and the clamp. If it had been desirable to make a rapid transition from the first to the second fluid she would have initially squeezed the fluid in the reservoir back into the first container before applying the clamp and connecting the supplementary set.

If a clamp is applied to the closable tube a considerable pressure can be generated in the reservoir when it is squeezed. This increase in pressure however does not increase the flow as it is also transmitted via the air contained in the upward extension of the reservoir and the air channel leading from it to the air-tight chamber surrounding the barostat device. The barostat device thus continues to maintain a constant flow even when the reservoir pressure is abnormally high. The junction between the upward extension of the reservoir with the air channel is arranged to have a closable region and to lie either behind or in front of the closable part of the closable tube leading from the piercing needle. This closable region is made so that it can flatten and become completely closed when included in the clamp used to close the closable tube or more simply when these two structure are gripped between finger and thumb. Under these circumstances, when the fluid inlet to the reservoir and the air inlet to the air channel are both closed, squeezing the reservoir greatly increases the flow through the administration set. This manoeuvre is useful when priming the set with fluid and can be performed repeatedly in an emergency to, in effect, pump the fluid when a very rapid infusion is needed. A less dramatic increase in flow can be obtained when using a collapsible container by squeezing the air from the air-tight chamber and placing a clamp on the closable region of the air channel. This completely inactivates the barostat device and will also enable the flow to be further increased by surrounding the collapsible container with a conventional blood bag pressurising device.

In an alternative fourth aspect of the invention the drip-chamber is placed up-stream of the regulator and barostat device so that it can be raised to a slightly more convenient height and if it is also made from flexible material there is the further advantage that should it contain an excessive amount of air this excess may be squeezed back into the reservoir and container in a controlled way after first closing the regulator.

Figures 5, 6:
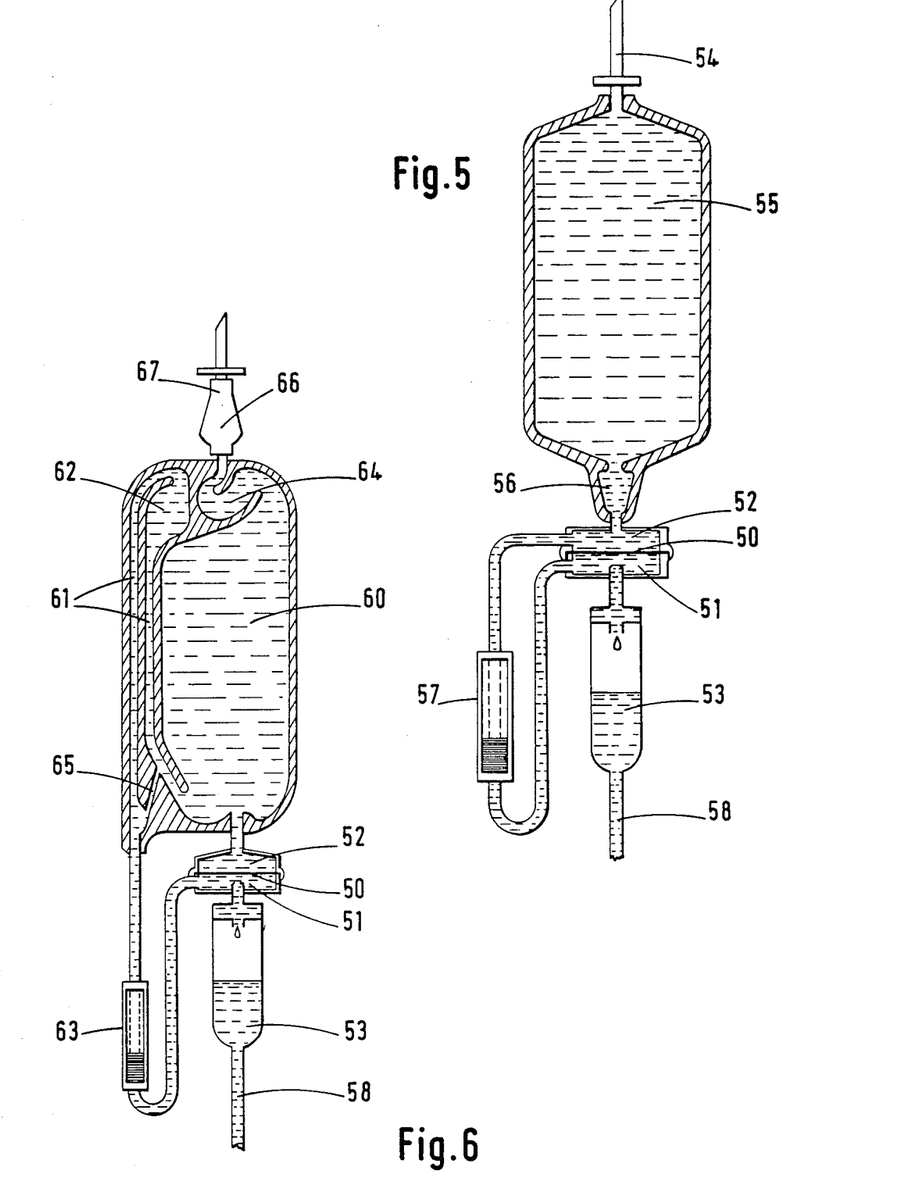
FIG. 5 shows a similar view of an administration set according to a fifth aspect of the invention.
FIG. 6 shows a similar view of an alternative embodiment of an administration set according to a fifth aspect of the invention.

In another aspect the present invention modifies the administration set hereinbefore described by using a barostat device that maintains at its inlet a pressure that is significantly lower than the controlling pressure and has as its controlling pressure the pressure generated by the whole column of fluid extending above it. This form of barostat device requires an elastic element acting on the flexible element to oppose the force of the controlling presure. Such a barostat device usually consists of two rigid chambers separated by an elastic diaphragm which combines the elastic and flexible elements. One of the chambers, the controlling chamber, is in communication with the fluid column upstream of the regulator and the other, the flow chamber, receives the infusion fluid after it has passed through the regulator. The fluid then leaves the flow chamber through a centrally placed outlet orifice that is near to the diaphragm. The pressure in the flow chamber becomes reduced compared with that in the control chamber because of the resistance to the flow imposed by the regulator. This reduced pressure in the flow chamber thus causes the elastic diaphragm to come nearer to the outlet orifice and to impede the flow to the outlet so preventing any further reduction of the pressure. The fluid in the flow chamber is thus maintained at a pressure which is lower than the controlling pressure by a constant amount that is determined by the elasticity of the diaphragm and the structural dimension of the device. This constant pressure difference across the regulator provides a constant flow even through the controlling pressure falls as the fluid container and then the reservoir empty. This type of barostat device cannot prevent the reservoir from emptying completely and so to ensure that air does not then enter the rest of the administration set a collapsible segment or other suitable device is placed in the outlet at the lowest part of the reservoir. Alternatively if the reservoir is of the collapsible type placing the collapsible region at its inlet could prevent the inflow of air and serve essentially the same purpose. Embodiments of this aspect of the invention are illustrated in FIGS. 5 and 6 described below.

According to this fifth aspect of the present invention there is provided an administration set made substantially in any of the ways described in the four previous aspects in which the flexible element of the barostat device is influenced by an elastic element and caused by the pressure of the fluid upstream of the regulator to offer the amount of resistance to the flow through the device that is required to maintain a pressure at its inlet downstream of the regulator that is lower by a constant amount than the pressure upstream of the regulator and the reservoir is given suitable means for preventing it from becoming completely empty of fluid.

When the administration set provided by the first aspect of the invention is modified to receive this type of barostat device the reservoir is provided with a collapsible region at its inlet or outlet. The fluid leaving the reservoir is most conveniently led through the control chamber to the regulator. The fluid then flows from the regulator to the inlet of the flow chamber and passes between the rim of the outlet orifice and the elastic diaphragm to enter the infusion tube. As before the drip chamber may be placed either upstream of the regulator or downstream of the barostat device. This relatively simple form of the invention has the advantage that the flow remains constant, even when a collapsible container is used, but the disadvantage that the reservoir empties more rapidly and should therefore be made larger.

When this type of barostat device is used with the administration sets made according to the other aspects of the invention there is no need for an air containing space in the upper part of the reservoir and an air channel to convey this pressure to the flexible element. The control chamber is connected to, or becomes part of, the outlet passage from the reservoir which then ascends to a a collapsible segment placed at approximately the same level as the reservoir inlet. The outlet passage descends again and there is a resistive pathway joining the ascending part to the descending part. On leaving this outlet passage the fluid flows through the regulator and then the flow chamber. When the reservoir starts to empty the collapsible segment in the outlet passage closes and all the flow is diverted to the resistive pathway which is now the only means of ensuring that the reservoir empties slowly. Means are again provided to prevent the reservoir from becoming completely empty. As this type of barostat device is relatively unaffected by changes in the back pressures from the veins there is no need for a collapsible tube to be placed downstream from it.

Suitably the components of the administration sets of the present invention are formed from polymer material which may be sealed to itself or another suitable polymer by heat or RF welding. Suitable polymers include plasticised polyvinyl chloride, which is commonly used to form fluid containers and tubing and the like for medical uses. A sheet of the polymer is suitably placed on a shaped metal former, having the required pattern of grooves and when necessary the sheet is pulled into close contact with the metal former and into the grooves using a vacuum, and then a second sheet of polymer is sealed to the first in the required manner. The components of the administration set may be assembled and sealed together so that the fluid reservoir and barostat are formed as one piece. Where necessary openings for tubes, inlets and outlets and the resistive pathway are formed by including metal rods of the appropriate diameter in the sealing process and then removing the rods and sealing the tubes etc into the spaces left subsequently.

The present invention also provides a fluid reservoir and barostat device suitable for use with a flow regulator, said fluid reservoir and barostat device being as herein before described.

BRIEF DESCRIPTION OF THE DRAWINGS

Preferred embodiments of the invention will now be described by way of example and with reference to the accompanying drawings in which.

DETAILED DESCRIPTION OF THE PREFERRED EMBODIMENTS

In FIG. 1 reservoir (1) is formed by heat-sealing together two sheets of approximately 0.4 millimeter thick plasticised PVC sheet in a similar way to that used for making the conventional type of collapsible fluid container. This reservoir (1) may have a capacity of about thirty milliliters. An approximately twenty-five centimeter length of tubing (2) connects a conventional type of piercing needle (3) to the upper end of the reservoir (1). Another length of tubing (4) passes from the outlet at the lower end of the reservoir (1) and incorporates the flow regulator (5) which may be a typical roller-clamp or some other more complex device. Either before or after the regulator (5) the tubing (4) is bent through 180 degrees so that it ascends to the region of the outlet of the reservoir (1) and there enters the barostat device (6). The barostat device (6) is made by the same radio-frequency heat-sealing methods as the reservoir (1) but from thinner 0.15 millimeters thick PVC sheet. An inverted V-shaped collapsible passageway is made by first gently folding the thin PVC sheet, then sealing the two leaves together along a line which crosses the fold at an acute angle of about thirty degrees and making a triangular-shaped seal within the acute angle with two sides parallel to the first seal and the fold but asymmetrically displaced so that the distance between the first seal and the triangle is about one centimeter and that between the folded edge and the triangle is about five millimeters. The length of both limbs of the passageway is about two centimeters. The fluid enters along the wide limb (7) and leaves by the narrow limb (8). The fold helps to prevent the narrow limb (8) from collapsing when the internal pressure becomes subatmospheric and the collapse is caused to occur at the junction of the two limbs in the apex of the inverted V-shape. Care is taken that both leaves are held perfectly flat during the sealing process and that no beads of molten PVC prevent the passageway from being completely occluded by the collapse. The passageway serves both as the functional part of the barostat device (6) and as a means of turning the direction of flow through another 180 degrees. A short tube (9) passes from the outlet of the barostat device downwards to the inlet of a conventional drip-chamber (10). The somewhat delicate barostat device is protected and supported by being placed in a pocket (11) formed beside and of the same material as the reservoir (1). The barostat device (6) is held securely in this pocket (11) by means of a combined heat seal that incorporates the thin PVC sheet of the device (6), the inlet and outlet tubes and the thicker sheet from the reservoir. A small hole (13) is made in the thicker outer sheet in order to make sure that the thin walls of the barostat device (6) are in equilibrium with the atmospheric pressure. A long infusion tube (12) leads from the outlet of the drip-chamber (10) to the usual type of rubber injection site and a luer fitting for connecting it to the cannula.

This improved administration set is used in a similar way to the conventional set except that the fluid container is allowed to empty completely before being replaced by a full one. The reservoir maintains the infusion and the nurse can make the replacement when convenient. If the flow rate becomes reduced she can test for a seriously raised back-pressure by squeezing the barostat device between the finger and thumb. A back pressure causes distention of the barostat device and when it is squeezed this distending fluid is forced into the drip-chamber. On release of the squeeze this fluid is replaced by reverse flow that causes air to pass up through the drip-tube. The upwards movement of air from the drip-chamber provides the clearest indication of a high back-pressure and warns the nurse to inspect the infusion tube and cannulation site.

In the administration set shown in FIG. 2 the fluid reservoir (14) is made, as before, by sealing together two sheets of plasticised PVC in a radio-frequency welding machine. One of the electrodes used in the machine has grooves from which the air is sucked with a powerful pump and the PVC sheet adjacent to this electrode is drawn into these grooves. When the seal is made with the other sheet along the edges of such a groove a tubular structure of D-shaped cross-section is formed. Two of these tubular structures (15, 16) are formed along one edge of the reservoir and arranged so that they become the by-pass tube (15) and the fluid passageway (16) of the reservoir inlet. On the other side of the reservoir another groove forms the air channel (17) which passes from the top of the reservoir to an air-tight chamber (18) that contains the barostat device (19) to be described hereinafter. The outlet of the by-pass tube (15) is connected by way of a -flow regulator (22) to the inlet of the barostat device (19), while the outlet of the barostat device (19) leads to a drip-chamber (23).

The groove in the electrode that forms the uppermost part of the by-pass tube (15) is widened and filled flush for a short distance with a hard epoxy resin which causes the tube to be flattened and become the collapsible segment (20). Before the two PVC sheets are sealed together a thin, approximately 0.25 mm, stainless steel wire is inserted between them and caused to lie across the region will separate the bottom of the reservoir (14) from the lower end of the by-pass tube (15). The wire is withdrawn after the sealing process and leaves a fine passage (21) about two centimeters in length that becomes the resistive pathway through which fluid leaves the reservoir (14) when the container is empty. When the reservoir is distended with fluid its edges may be distorted and cause kinking of the tubular structures. This distortion can be considerably reduced by cutting a hollow, or series of grooves, in the recessed reservoir-forming part of the suction electrode. The suction draws the PVC sheet into the hollow or grooves before the edges are sealed and this causes a fullness in the shape of this wall of the reservoir that accomodates the fluid more easily.

The barostat device (19) shown enlarged in FIG. 2a is extended to also form the collapsible tube (26) downstream of its outlet aperture (45). They are made by the same method of radio-frequency sealing of approximately 0.15 mm PVC sheet to form an inverted V-shaped collapsible passageway shown in FIG. 1 but from two separate sheets rather than by folding one sheet. The ascending entry limb (27) is narrow, the descending limb is about 1 cm wide and extended to be about 3 cm long. The inlet (44) and outlet (45) apertures are made in the conventional way by inserting metal mandrils and using appropriately shaped electrodes to make the combined seal with the thicker material. This seal completes the air-tight chamber (18), and is only about 5 mm below the apex of the inner triangular-shaped seal. The collapse of the passageway is now caused to occur just above the outlet aperture (45). The longer descending limb extends beyond this outlet aperture and forms the collapsible tube (26). The collapsible tube (26) is protected by a pocket (28) of the thicker PVC material and another combined seal is formed to seal it to its outlet tube and the thicker material. Care is taken to leave a hole (29) somewhere in this pocket (28) so that the walls of the collapsible tube are always exposed to the relatively unchanging pressure of the atmosphere. The air-tight chamber (18) changes shape as the pressure in it changes and the flexible walls of the collapsible passageway of the barostat (19) are hardly affected by these changes because the passageway is in the form of an inverted V or U. If the collapsible passageway were to pass from one end of the air-tight chamber to the other, in a form similar to the collapsible tube (26) in its pocket, the passageway would be severely affected by the changing shape of the air-tight chamber and its compensating function would be upset.

The collapsible tube may be provided down-stream of the barostat device and drip-chamber. This collapsible tube may be in the form of a 35 centimeter length of lay-flat tubing (not shown) approximately one centimeter wide, made from 0.15 millimeter thick plasticised medical grade PVC material, and is connected to the outlet of the drip-chamber (23) and conveys the fluid to the infusion tube and so on to the patent. Care is taken to make the tube so that it will collapse completely when the pressure inside becomes less than outside. For example, if the edges are folded they must be pressed absolutely flat or if they are formed by welding these welds must be free from beads that could hold the internal surfaces slightly apart. This long form of the collapsible tube is used to measure the back-pressure from the veins as previously described. When it is employed there is no need for the short form of the collapsible tube (26) in the pocket (28) immediatey down-stream of the barostat device (19).

In the administration set shown in FIGS. 3 and 4 the reservoir (30), barostat device (31) in the air-tight chamber (32) and the short collapsible tube (26) in the pocket (34) are made by the same methods as are described in the second embodiment and shown in FIG. 2 and 2a. The piercing needle (35) however connects with a short closable tube (48) and injection site (36) made of rubber with a conical expansion in its mid region of the type frequently used as an injection site at the termination of the infusion tube of administration sets where they lead to the connector for the cannula. The other end of this short closable tube (48) directly enters the main body of the reservoir (30) by a secure seal. One side of the top of the reservoir extends up in a curving manner (37) to lie in front of a closable portion of the closable tube (48) and there joins the air channel (46) that leads down to the air-tight chamber (32) as in the previous embodiment. The groove in the forming electrode that shapes this junction of the curving extension of the reservoir (37) with the air channel (46) is filled with a hard epoxy resin and contoured in such a way that the junction region (33) so formed normally remains open to the passage of air but is closable and can be completely closed by for example squeezing it together with the closable portion of the closable tube (48) between the finger and thumb. In FIG. 3 an outlet passage (38) leads from the bottom of the reservoir (30) as an ascending part to a collapsible region (47) formed by widening the groove in the electrode and filling it flush for a short distance with epoxy resin. On leaving the collapsible region (47) the outlet passage (38) descends to an outlet tube (39) that leads to the regulator (40) and barostat device (31). A resistive pathway (41) is formed between the ascending and descending parts of the outlet passage (38) by introducing a fine stainless steel wire of approximately 0.25 mm diameter between the two PVC sheets across the region between these parts of the outlet passage and then withdrawing the wire after sealing to leave the pathway. The drip chamber (42) is placed either in the infusion tube (43) down-stream of the barostat device or in the outlet tube (39) up-stream of the regulator (40). If in the second position up-stream of the regulator as shown in FIG. 4 the drip chamber (42) should preferably be made of a semi-flexible material so that should it contain an excessive amount of air this excess may be squeezed back into the reservoir after having temporarily closed the regulator (40).

In the administration sets shown in FIGS. 5 and 6 the barostat device 49 is moulded in a rigid plastics material such as unplasticised PVC and made in two halves each having the shape of a shallow circular dish. The elastic diaphragm (50) is made from a thin sheet of a suitable rubbery material such as silicone rubber with thickness of 0.3 mm and a diameter of 2 cm (approx.). This is represented as being larger in the figures for the sake of clarity. The rim of the lower dish-shaped moulding is made to fit into a small recess in the rim of the upper moulding. The elastic diaphragm is laid across the rim and recess of the upper moulding and the lower moulding pushed into the recess so gripping the diaphragm to make a water-tight seal and also putting it into a slight degree of tension. The two mouldings are then fixed securely together by ultrasonically welding four lugs, not shown, or by some other means suited to the mode of assembly. The lower moulding encloses the flow chamber (51) and has a precisely formed outlet orifice with its upper edge positioned 1.4 mm below the plane of the rim and an inlet tube entering at the side. The upper moulding encloses the control chamber (52) and has a central inlet tube and in the form shown in FIG. 5 also a side tube providing an outlet. The outlet orifice in the flow chamber (51) leads to the drip-tube in the drip-chamber (53) and the lower moulding may be made as part of the moulding that forms the top of the drip-chamber. In the administration set shown in FIG. 5 the piercing needle (54) is connected to the reservoir (55) which is made by sealing together two sheets of about 0.4 mm thick plasticised PVC material as in the previous embodiments. A collapsible segment (56) is formed just above the outlet by filling the groove in the forming electrode as before with epoxy resin and milling it flush with the surface of the electrode. A length of PVC tube connects the outlet of the control chamber (52) with the inlet of the flow chamber (51) and is fitted with a rollerclamp (57) or more elaborate type of regulator. The fluid leaving the drip-chamber (53) passes into the infusion tube (58).

The reservoir (60) of the administration set shown in FIG. 6 has an outlet passage (61) that ascends to a collapsible segment (62) and then descends to the tube bearing the regulator (63). There is another collapsible segment (64) at the inlet to the reservoir. When the container has become empty both of these collapsible segments (62) (64) close as the pressure in the top of the reservoir falls below the atmospheric pressure. The reservoir can now only empty through the resistive pathway (65) which is made to be about 0.20 mm in diameter by the same method as before and can prolong the infusion by several hours. If the reservoir should be allowed to become completely empty the collapsible segment (64) at its inlet will prevent air from entering the set. A closable tube (67) and injection site (66) is included downstream of the piercing needle as in some of the previous embodiments. The barostat device can be inactivated as in some previous embodiments by closing the part of the reservoir leading to the control chamber (52) with a clamp or between the finger and thumb.

I claim:
1. An administration set, comprising:
   (A) a principal liquid inlet adapted to receive liquid gravitationally from a source of liquid;
   (B) a principal outlet adapted to enable liquid to flow gravitationally from the set in a controlled manner;
   (C) a reservoir communicating with said principal inlet and itself having a outlet;
   (D) a flow regulator with an inlet and an outlet and operative to regulate the flow of liquid flowing through it from its inlet to its outlet;
   (E) a barostat comprising
      (i) a flow chamber with an inlet and an outlet,
      (ii) wall means bounding at least part of said chamber and having an inner surface and an outer surface, the wall means being movable between a closed position in which it prevents the flow of liquid through the flow chamber from the inlet thereof and an open position in which it does not prevent such a flow of liquid,
      (iii) the position of the wall means being determined by the difference between the pressure of liquid in the flow chamber and applied to the inner surface of the wall means and a fluid pressure applied to the outer surface of the wall means;
   (F) the outlet of the reservoir communicating with the inlet of the flow regulator;
   (G) the outlet of the flow regulator communicating with the inlet of the flow chamber; and
   (H) the outlet of the flow chamber communicating with the principal outlet.

2. An administration set according to claim 1 in which the fluid pressure applied to the outer surface of the wall means is atmospheric pressure.

3. An administration set according to claim 2 in which the outlet of the reservoir and the inlet of the flow chamber of the barostat are at substantially the same level, the arrangement being such that in use liquid ceases to flow from the set before the reservoir is completely empty.

4. An administration set according to claim 1 in which there is an upper part of the reservoir above the liquid surface in which in use air is trapped, an air tight chamber which contains the flow chamber of the barostat and an air channel which communicates between the airtight chamber and the upper part of the reservoir, the outer surface of the wall means being subject to the fluid pressure of the air in the air tight chamber, the arrangement being such that in use, while the reservoir remains full and the source of liquid progressively empties, the liquid pressure of the liquid in the reservoir falls, the air pressure applied to the outer surface of the wall means of the flow chamber also falls and the pressure at the inlet of the flow chamber falls to a similar extent.

5. An administration set according to claim 4 in which the upper part of the reservoir in which air is trapped is flexible and resilient and is accessible so that it can be amnually squeezed to close off communication to the air tight chamber temporarily.

6. An administration set according to claim 5 in which the principal inlet also includes a flexible and resilient closable tube alongside said upper part of the reservoir, so that said closable tube and said upper part of the reservoir can both be closed by a single manual squeezing action.

7. An administration set according to claim 4 in which there is a collapsible tube below the barostat, the collapsible tube having an inlet communicating with the outlet of the flow chamber of the barostat and operative to collapse, to restrict liquid flow therethrough, when the pressure in the collapsible tube falls below atmospheric pressure and with an outlet communicating with the principal outlet.

8. An administration set according to claim 4 in which the outlet of the reservoir and the inlet of the flow chamber of the barostat are at substantially the same level, the arrangement being such that in use liquid ceases to flow from the set before the reservoir is completely empty.

9. An administration set according to claim 1 in which in use the fluid pressure applied to the outer surface of the wall means is the pressure of liquid in the reservoir.

10. An administration set according to claim 4 in which three is biasing means associated with the wall means operative to bias the wall means towards its open position.

11. An administration set according to claim 10 in which at least part of the wall means is elastic, the biasing means being constituted by the innate elasticity thereof.

12. An administration set according to claim 1 in which there is an outlet tube having a collapsible segment and having an inlet and an outlet below the level of the collapsible segment, the inlet of the outlet tube communicating with the outlet of the reservoir and the outlet of the outlet tube communicating with the inlet of the flow regulator said collapsible segment comprising a flexible wall portion operative to flex and close the outlet tube so that in use the flexible wall portion closes the tube when the level of the liquid in the reservoir falls below the level of the upper part of the tube and a constricted passageway constituting a by-pass of the collapsible segment so that the liquid can flow from the reservoir through the passageway to the flow regulator, at a reduced rate when the reservoir is emptying.

13. An administration set according to claim 12 in which the pricipal inlet communicates directly with an upper part of the reservoir.

14. An administration set according to claim 12 in which the principal inlet communicates directly with the outlet tube at a location such that in use liquid flowing from the principal inlet to the outlet of the outlet tube passes through said collapsible segment.

15. An administration set according to claim 1 in which the principal inlet includes a flexible and resilient closable tube which can be manually squeezed to close the principal inlet temporarily.

16. An administration set according to claim 15 in which said reservoir is normally vertical and has upper and lower parts and there is an injection site between said closable tube and upper part of the reservoir.

17. An administration set according to claim 1 in which the wall means of the flow chamber of the barostat is made from a thin flexible material.

18. An administration set according to claim 17 in which the said wall means is arranged to provide the walls of a flow chamber which is substantially in the form of an inverted V-shape.

19. An administration set according to claim 1 in which the reservoir and the barostat constitute portions of a single component of the administration set.

20. An admministration set according to claim 1 in which there is additionally present a drip chamber communicating with the outlet of the flow chamber of the barostat and the principal outlet.

21. An administration set according to claim 1 in which there is additionally present a drip chamber communicating with the outlet of the reservoir and the inlet of the flow regulator.

* * * * *